United States Patent
Chen et al.

(10) Patent No.: US 7,319,781 B2
(45) Date of Patent: Jan. 15, 2008

(54) METHOD AND SYSTEM FOR MULTIPLE PASSES DIAGNOSTIC ALIGNMENT FOR IN VIVO IMAGES

(75) Inventors: Shoupu Chen, Rochester, NY (US); Lawrence A. Ray, Rochester, NY (US); Nathan D. Cahill, West Henrietta, NY (US); Marvin M. Goodgame, Ontario, NY (US)

(73) Assignee: Carestream Health, Inc., Rochester, NY (US)

( * ) Notice: Subject to any disclaimer, the term of this patent is extended or adjusted under 35 U.S.C. 154(b) by 701 days.

(21) Appl. No.: 10/679,712

(22) Filed: Oct. 6, 2003

(65) Prior Publication Data

US 2005/0074151 A1 Apr. 7, 2005

(51) Int. Cl.
*G06K 9/00* (2006.01)
*G06K 9/32* (2006.01)
*A61B 1/00* (2006.01)

(52) U.S. Cl. ............... 382/128; 382/294; 600/101

(58) Field of Classification Search ........ 382/128–132, 382/294, 305; 348/65, 45, 72; 356/241.1; 600/109, 112, 111, 424, 310; 396/427
See application file for complete search history.

(56) References Cited

U.S. PATENT DOCUMENTS 5,604,531 A  2/1997  Iddan et al.
6,909,794 B2 *  6/2005  Caspi .................... 382/128
6,950,690 B1 *  9/2005  Meron et al. ............ 600/424
2003/0023150 A1  1/2003  Yokoi et al.
2003/0085994 A1  5/2003  Fujita et al. .............. 348/77

FOREIGN PATENT DOCUMENTS

EP          1 238 624 A2    11/2002
EP          1 260 176 A2    11/2002
WO         WO 00/22975      4/2000
WO         WO 02/054932 A2  7/2002

\* cited by examiner

*Primary Examiner*—Samir Ahmed
*Assistant Examiner*—Jayesh A Patel

(57) ABSTRACT

A digital image processing method for multiple passes diagnostic alignment of in vivo images, comprising the steps of: acquiring images using an in vivo video camera system; forming an in vivo video camera system examination bundlette; transmitting the examination bundlette to proximal in vitro computing device(s); processing the transmitted examination bundlette; automatically identifying abnormalities in the transmitted examination bundlette; and setting off alarm signals to a local site provided that suspected abnormalities have been identified for each pass forming a registration bundle; selecting identification elements of an image from the registration bundle of one pass; and retrieving corresponding images from another pass.

9 Claims, 13 Drawing Sheets

METHOD AND SYSTEM FOR MULTIPLE PASSES DIAGNOSTIC ALIGNMENT FOR IN VIVO IMAGES

FIELD OF THE INVENTION

The present invention relates generally to an endoscopic imaging system and, in particular, to multiple passes diagnostic alignment for in vivo images.

BACKGROUND OF THE INVENTION

Several in vivo measurement systems are known in the art. They include swallowed electronic capsules which collect data and which transmit the data to an external receiver system. These capsules, which are moved through the digestive system by the action of peristalsis, are used to measure pH ("Heidelberg" capsules), temperature ("CoreTemp" capsules), and pressure throughout the gastrointestinal (GI) tract. They have also been used to measure gastric residence time, which is the time it takes for food to pass through the stomach and intestines. These capsules typically include a measuring system and a transmission system, wherein the measured data is transmitted at radio frequencies to a receiver system.

U.S. Pat. No. 5,604,531, issued Feb. 18, 1997 to Iddan et al., titled "In Vivo Video Camera System" teaches an in vivo measurement system, in particular an in vivo camera system, which is carried by a swallowed capsule. In addition to the camera system there is an optical system for imaging an area of the GI tract onto the imager and a transmitter for transmitting the video output of the camera system. The overall system, including a capsule that can pass through the entire digestive tract, operates as an autonomous video endoscope. It images even the difficult-to-reach areas of the small intestine.

U.S. Patent Application No. 2003/0023150 A1, filed Jul. 25, 2002 by Yokoi et al., titled "Capsule-Type Medical Device And Medical System" teaches a swallowed capsule-type medical device which is advanced through the inside of the somatic cavities and lumens of human beings or animals for conducting examination, therapy, or treatment. Signals including images captured by the capsule-type medical device are transmitted to an external receiver and recorded on a recording unit. The images recorded are retrieved in a retrieving unit and displayed on the liquid crystal monitor to be compared by an endoscopic examination crew with past endoscopic disease images that are stored in a disease image database.

The examination requires the capsule to travel through the GI tract of an individual, which will usually take a period of many hours. A feature of the capsule is that the patient need not be directly attached or tethered to a machine and may move about during the examination. While the capsule will take several hours to pass through the patient, images will be recorded and will be available while the examination is in progress. Consequently, it is not necessary to complete the examination prior to analyzing the images for diagnostic purposes. However, it is unlikely that trained personnel will monitor each image as it is received. This process is too costly and inefficient. However, the same images and associated information can be analyzed in a computer-assisted manner to identify when regions of interest or conditions of interest present themselves to the capsule. When such events occur, then trained personnel will be alerted and images taken slightly before the point of the alarm and for a period thereafter and the images can be given closer scrutiny.

Another advantage of this system is that trained personnel are alerted to an event or condition that warrants their attention. Until such an alert is made, the personnel are able to address other tasks, perhaps unrelated to the patient of immediate interest.

Using computers to examine and to assist in the detection from images is well known. Also, the use of computers to recognize objects and patterns is also well known in the art. Typically, these systems build a recognition capability by training on a large number of examples. The computational requirements for such systems are within the capability of commonly available desk-top computers. Also, the use of wireless communications for personal computers is common and does not require excessively large or heavy equipment. Transmitting an image from a device attached to the belt of the patient is well-known.

In general, multiple passes of in vivo imaging are required for a patient in a course of disease diagnosis and treatment. The progress of the disease and the effectiveness of the treatment are evaluated by examining corresponding in vivo images captured in different passes. Notice that, using this type of capsule device, one pass of imaging could produce thousands and thousands of images to be stored and visually inspected by the medical professionals.

Notice also that U.S. Patent Application Publication No. 2003/0023150 teaches a method of storing the in vivo images first and retrieving them later for visual inspection of abnormalities. The method taught by 2003/0023150 lacks of the abilities of automatic detection of abnormalities. Furthermore, the method lacks of the abilities of multiple passes registration (or diagnostic alignment) for corresponding in vivo image evoking. Obviously, the inspection method taught by 0023150 is far from efficient.

It is useful to design an endoscopic imaging system that is capable of detecting an abnormality automatically and aligning in vivo images from multiple passes.

There is a need therefore for an improved endoscopic imaging system that overcomes the problems set forth above and addresses the utilitarian needs set forth above.

These and other aspects, objects, features, and advantages of the present invention will be more clearly understood and appreciated from a review of the following detailed description of the embodiments and appended claims, and by reference to the accompanying drawings.

SUMMARY OF THE INVENTION

The need is met according to the present invention by providing a digital image processing method for aligning in vivo images from multiple passes of a gastrointestinal tract to aid in diagnostic gastrointestinal disease that includes conducting multiple passes of in vivo imaging within the gastrointestinal tract; forming a registration bundle of metadata for each of the multiple passes; selecting possible indexed features of an in vivo image from the registration bundle associated with one pass; and retrieving corresponding images from another pass based on prior selection of the possible indexed features.

BRIEF DESCRIPTION OF THE DRAWINGS

To facilitate understanding, identical reference numerals have been used, where possible, to designate identical elements that are common to the figures.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

During a typical examination of a body lumen, a conventional in vivo camera system captures a large number of images. The images can be analyzed individually, or sequentially, as frames of a video sequence. An individual image or frame without context has limited value. Some contextual information is frequently available prior to or during the image collection process; other contextual information can be gathered or generated as the images are processed after data collection. Any contextual information will be referred to as metadata. Metadata is analogous to the image header data that accompanies many digital image files.

Figure 1:
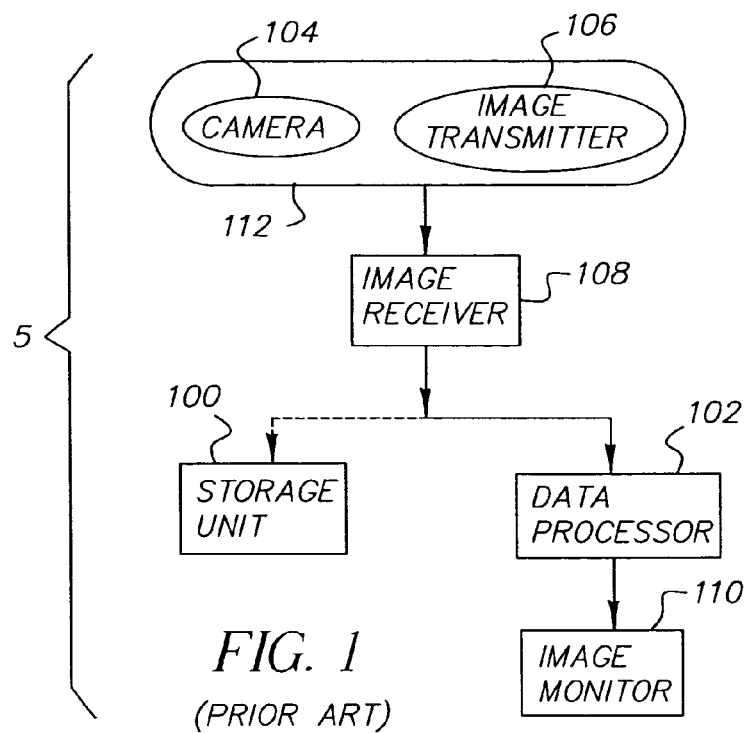
FIG. 1 is a prior art block diagram illustration of an in vivo camera system.

FIG. 1 shows a prior art block diagram of the in vivo video camera system 5 described in U.S. Pat. No. 5,604,531 (described previously). The in vivo video camera system 5 captures and transmits images of the GI tract while passing through the gastrointestinal lumen. The in vivo video camera system 5 includes a storage unit 100, a data processor 102, a camera 104, an image transmitter 106, an image receiver 108 which usually includes an antenna array, and an image monitor 110. Storage unit 100, data processor 102, image monitor 110, and image receiver 108 are located outside the patient's body. Camera 104, as it transits the GI tract, is in communication with image transmitter 106 located in capsule 112 and image receiver 108 located outside the body. Data processor 102 transfers frame data to and from storage unit 100 while the former analyzes the data. Data processor 102 also transmits the analyzed data to image monitor 110 where a physician views it. The data can be viewed in real-time or at some later date. Here, throughout this patent application, 'real-time' means that the abnormality detection process starts as soon as an in vivo image becomes available while the capsule 112 containing the imaging system is traveling throughout the body. There is no need to wait for the imaging system within the capsule to finish its imaging of the whole GI tract. Such 'real-time' imaging is different than capturing images in very short periods of time.

Figure 2A:
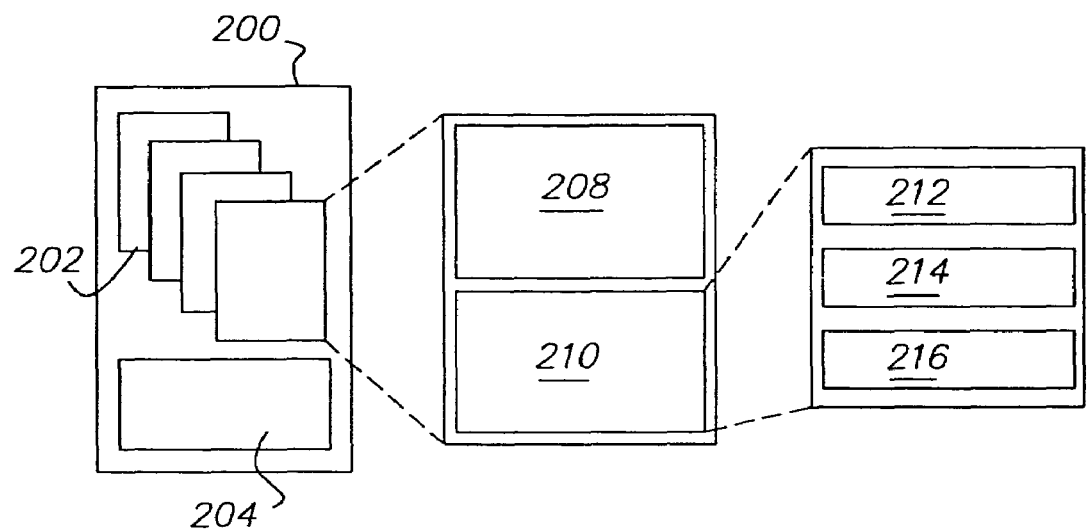
FIG. 2A is an illustration of the concept of an examination bundle of the present invention.

Referring to FIG. 2A, the complete set of all images captured during the examination, along with any corresponding metadata, will be referred to as an examination bundle 200. The examination bundle 200 consists of a plurality of individual image packets 202 and a section containing general metadata 204.

An image packet 202 comprises two sections: the pixel data or in vivo image 208 of an image that has been captured by the in vivo camera system, and image specific metadata 210. The image specific metadata 210 can be further refined into image specific collection data 212, image specific physical data 214, and inferred image specific data 216. Image specific collection data 212 includes information such as the frame index number, frame capture rate, frame capture time, and frame exposure level. Image specific physical data 214 includes information such as the relative position of the capsule 112 when the image was captured, the distance traveled from the position of initial image capture, the instantaneous velocity of the capsule 112, capsule orientation, and non-image sensed characteristics such as pH, pressure, temperature, and impedance. Inferred image specific data 216 includes location and description of detected abnormalities within the image, and any pathologies that have been identified. This data can be obtained either from a physician or by automated methods.

The general metadata 204 includes such information as the date of the examination, the patient identification, the name or identification of the referring physician, the purpose of the examination, suspected abnormalities and/or detection, and any information pertinent to the examination bundle 200. The general metadata 204 can also include general image information such as image storage format (e.g., TIFF or JPEG), number of lines, and number of pixels per line.

Figure 2B:
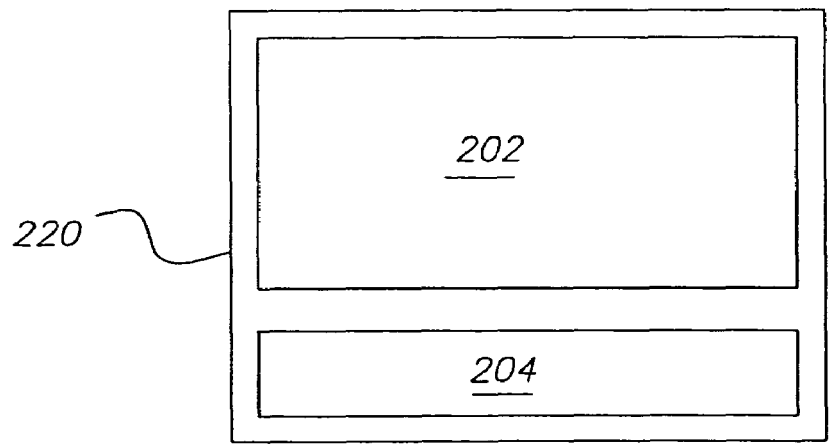
FIG. 2B is an illustration of the concept of an examination bundlette of the present invention.

Referring to FIG. 2B, a single image packet 202 and the general metadata 204 are combined to form an examination bundlette 220 suitable for real-time abnormality detection. The examination bundlette 220 differs from the examination bundle 200 in that the examination bundle 200 requires the GI tract to be imaged completely during travel of the capsule 112. In contrast, the examination bundlette 220 requires only a portion of the GI tract to be imaged as corresponding to the real-time imaging disclosed herein.

It will be understood and appreciated that the order and specific contents of the general metadata or image specific metadata may vary without changing the functionality of the examination bundle 200.

Figure 3:
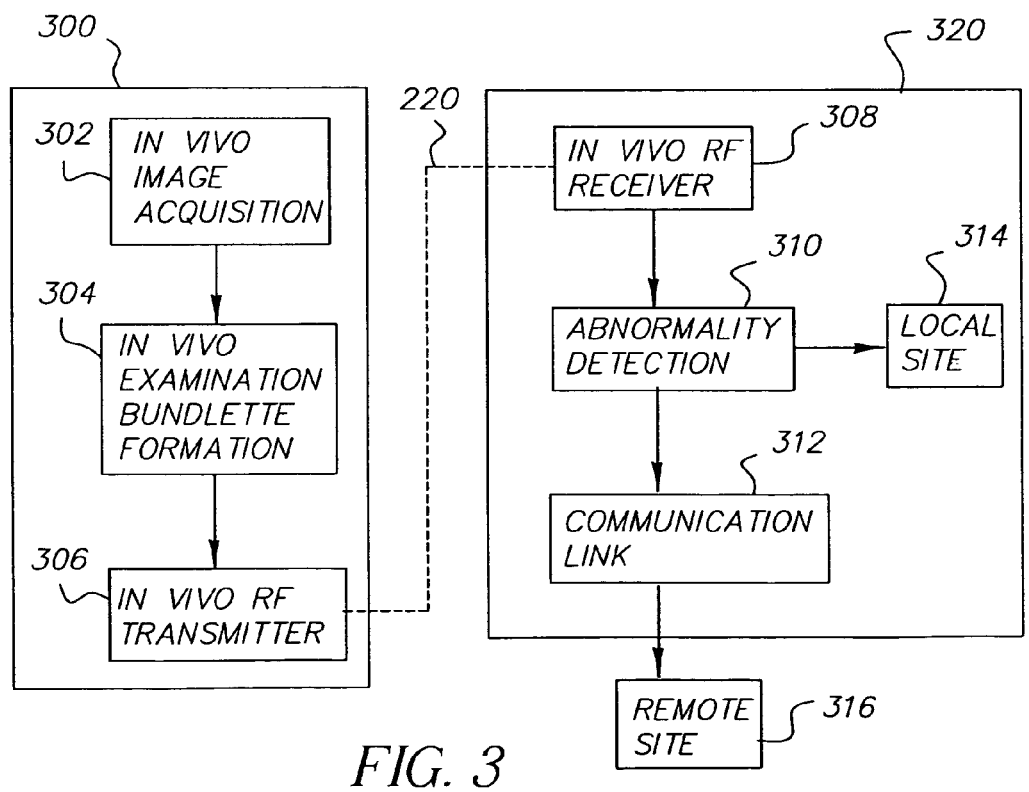
FIG. 3 is a flowchart illustrating information flow of the real-time abnormality detection method of the present invention.
Figure 4:
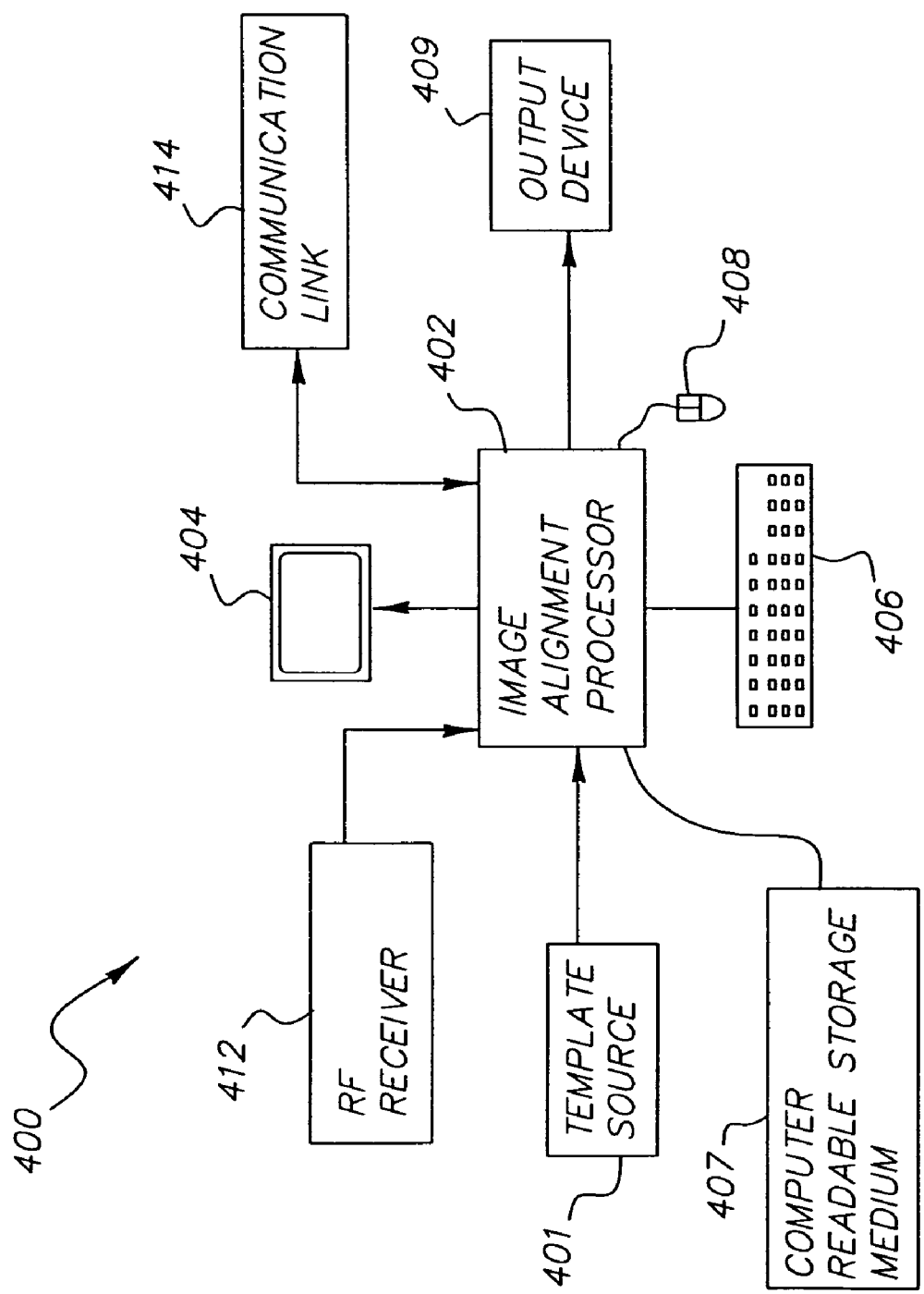
FIG. 4 is a schematic diagram of an examination bundlette processing hardware system useful in practicing the present invention.

Referring now to FIGS. 2A and 3, an exemplary embodiment of the present invention is described. FIG. 3 is a flowchart illustrating the real-time automatic abnormality detection method of the present invention. Later herein one exemplary embodiment, the real-time automatic abnormality detection will be used for a multiple passes diagnostic alignment. In FIG. 3, an in vivo imaging 25 system 300 can be realized by using systems such as the swallowed capsule described in U.S. Pat. No. 5,604,531 (previously described) for the present invention. An in vivo image 208, shown in FIG. 2A, is captured in an in vivo image acquisition step 302. During In Vivo Examination Bundlette Formation step 304, the image 208 is combined with image specific metadata 210 to form an 30 image packet 202, as shown in FIG. 2A. The image packet 202 is further combined with general metadata 204 and compressed to become an examination bundlette 220. The examination bundlette 220 is transmitted, through radio frequency, to a proximal in vitro computing device in RF transmission step 306. An in vitro computing device 320 is either a portable computer system attached to a belt worn by the patient or in near proximity to a patient. Alternatively, it is a system such as shown in FIG. 4 and will be described in detail later. The transmitted examination bundlette 220 is received in the proximal in vitro computing device 320 during an In Vivo RF Receiver step 308. Data received in the in vitro computing device 320 is examined for any sign of disease in an abnormality detection step 310. The step of abnormality detection 310 is further detailed in FIG. 5

Figure 5:
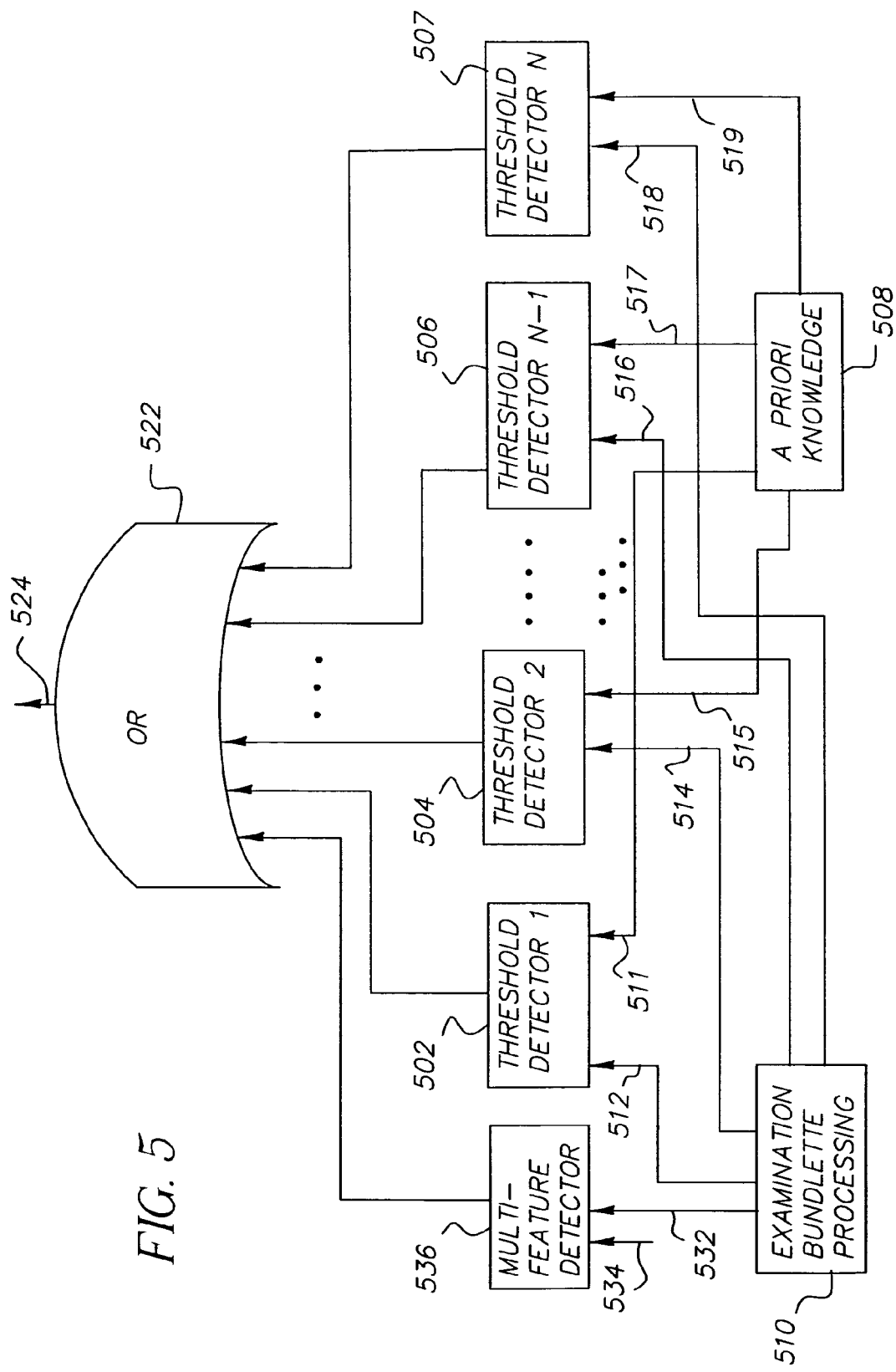
FIG. 5 is a flowchart illustrating abnormality detection of the present invention.

Referring to FIG. 5, the examination bundlette 220 is first decompressed, decomposed, and processed in the examination bundlette processing step 510. During the examination bundlette processing step 510, the image data portion of the examination bundlette 220 is subjected to image processing algorithms such as filtering, enhancing, and geometric correction. These algorithms can be implemented in color space or grayscale space. There are a plurality of threshold detectors, 502, 504, 506, and 507, each capable of handling one of the non-image sensed characteristics in the GI tract such as pH 512, pressure 514, temperature 516, and impedance 518. Distributions and thresholds of the non-image sensed characteristics such as pH 512, pressure 514, temperature 516, and impedance 518 are learned in a step of a priori knowledge 508. If values of the non-image sensed characteristics such as pH 512, pressure 514, temperature 516, and impedance 518 pass over their respective thresholds 511, 515, 517, and 519, corresponding alarm signals are sent to a logic OR gate 522. Also in FIG. 5, there is a multi-feature detector 536 which is detailed in FIG. 6.

Figure 6:
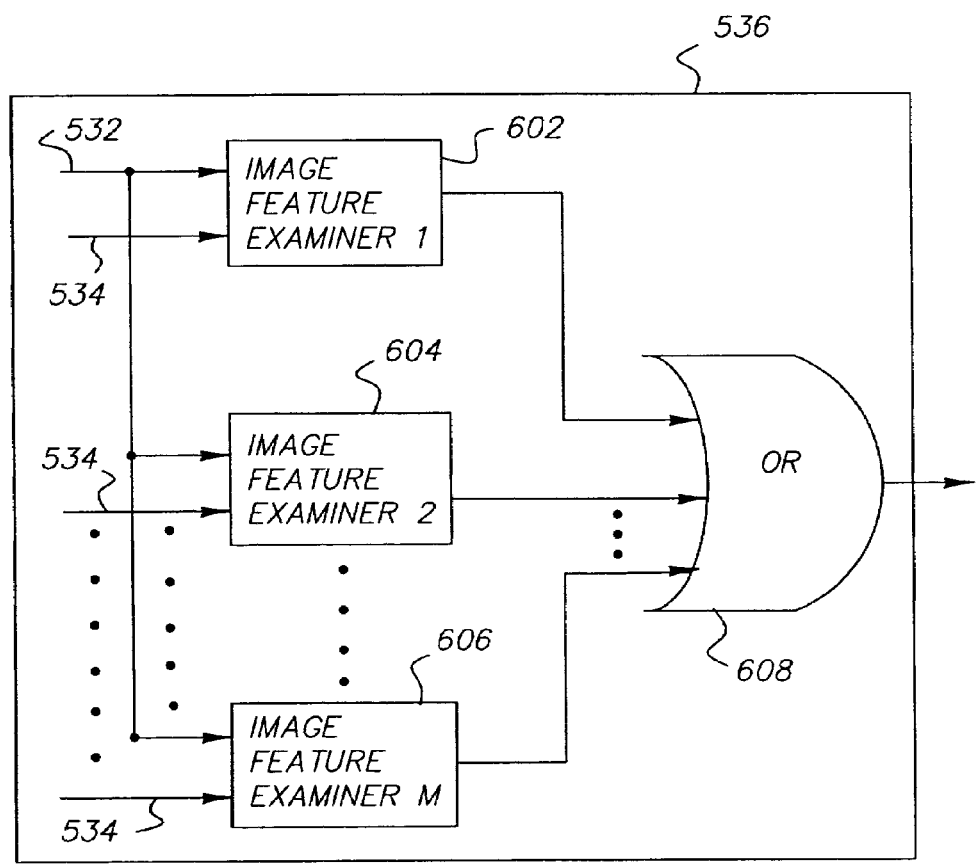
FIG. 6 is a flowchart illustrating image feature examination of the present invention.

Referring to FIG. 6, there is a plurality of image feature detectors, each of which examines one of the image features of interest. Image features such as color, texture, and geometric shape of segmented regions of the GI tract image 532 are extracted and automatically compared to predetermined templates 534 by one of the image feature examiners 602, 604, or 606. The predetermined templates 534 are statistical representations of GI image abnormality features through supervised learning. If any one of the multi-features in image 532 matches its corresponding template or within the ranges specified by the templates, an OR gate 608 sends an alarm signal to the OR gate 522, shown in FIG. 5.

Referring to FIGS. 5 and 3, any combination of the alarm signals from detectors 536, 502, 504, 506, and 507 will prompt the OR gate 522 to send a signal 524 to a local site 314 and to a remote health care site 316 through communication link 312. An exemplary communication link 312 could be a broadband network connected to the in vitro computing system 320. The connection from the broadband network to the in vitro computing system 320 could be either a wired connection or a wireless connection.

An exemplary image feature detection is the color detection for Hereditary Hemorrhagic Telangiectasia disease. Hereditary Hemorrhagic Telangiectasia (HHT), or Osler-Weber-Rendu Syndrome, is not a disorder of blood clotting or missing clotting factors within the blood (like hemophilia), but instead is a disorder of the small and medium sized arteries of the body. HHT primarily affects 4 organ systems; the lungs, brain, nose, and gastrointestinal (stomach, intestines, or bowel) system. The affected arteries either have an abnormal structure causing increased thinness or an abnormal direct connection with veins (arteriovenous malformation). Gastrointestinal tract (stomach, intestines, or bowel) bleeding occurs in approximately 20 to 40% of persons with HHT. Telangiectasias often appear as bright red spots in the gastrointestinal tract.

Figure 8A:
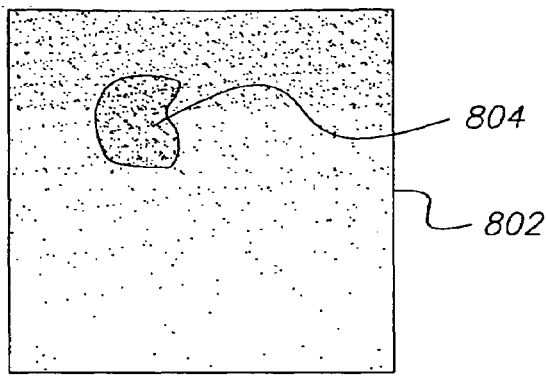
FIGS. 8A, 8B, 8C, and 8D are illustrations of four images related to in vivo image abnormality detection of the present invention.
Figure 8B:
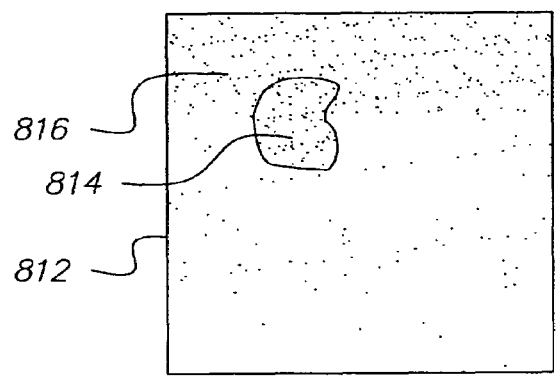
Figure 8C:
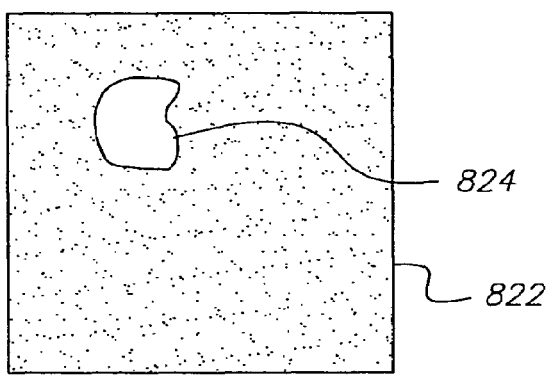
Figure 8D:
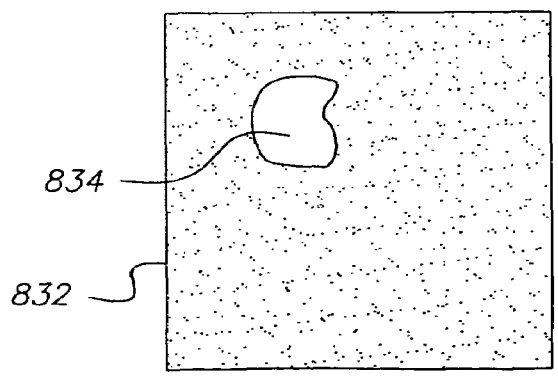

A simulated image of a telangiectasia 804 on a gastric fold is shown in image 802 in FIG. 8A. Note that the color image 802 is shown in FIG. 8A as a gray scale (black and white) image. To human eyes, the red component of the image provides distinct information for identifying the telangiectasia 804 on the gastric fold. However, for the automatic telangiectasia detection using a computer, the native red component alone as shown by red image 812 (FIG. 8B) of the color image 802, in fact, is not able to clearly distinguish the foreground (telangiectasia 814) and the part of the background 816 of image 812 in terms of pixel intensity values.

Figure 9:
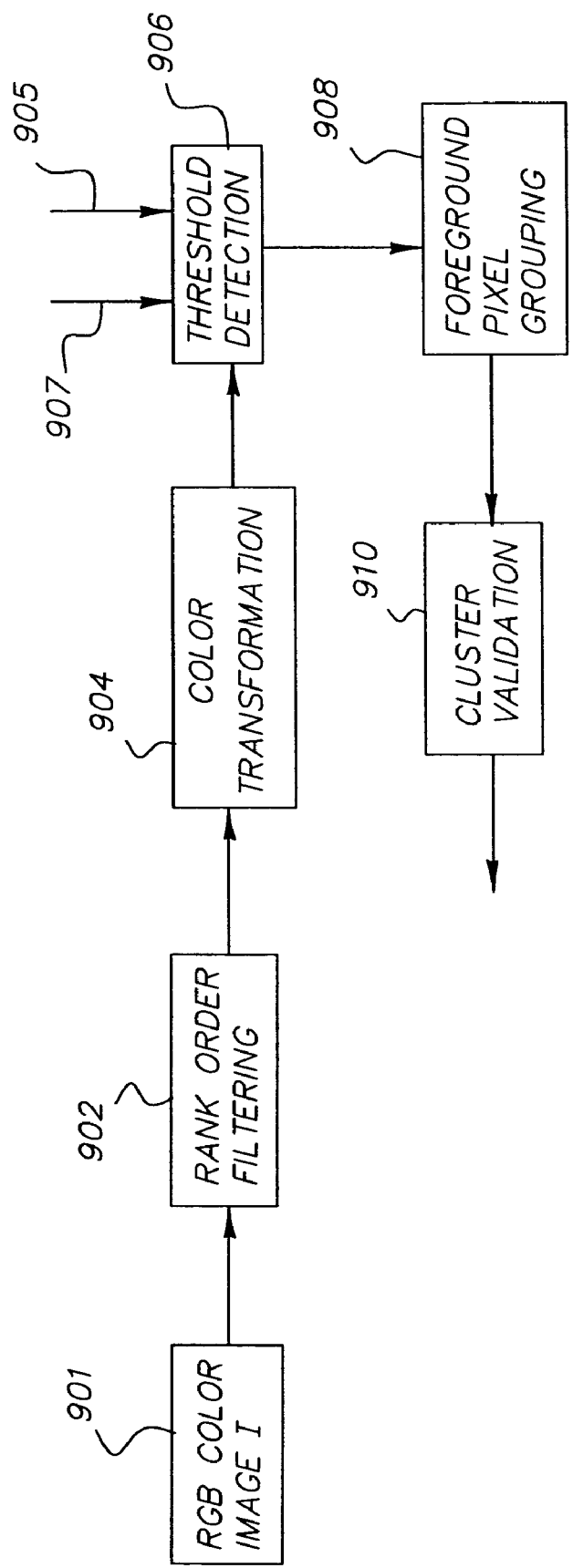
FIG. 9 is a flowchart illustrating color feature detection of the present invention.

To solve the problem, the present invention devises a color feature detection algorithm that detects the telangiectasia 804 automatically in an in vivo image. Referring to FIG. 9, the color feature detection performed according to the present invention by the multi-feature detector 536, shown in FIG. 5, will be described. The color digital image 901, expressed in a device independent RGB color space is first filtered in a rank order filtering step 902. One exemplary rank order filtering is median filtering. Denote the input RGB image by $I_{RGB} = \{C_i\}$, where i=1, 2, 3 for R, G, and B color planes respectively. Pixels at location (m, n) in a plane $C_i$ is represented by $p_i(m, n)$, where m=0, ... M−1 and n=0, ... N−1, M is the number of rows, and N is the number of columns in a plane. Exemplary values for M and N are 512 and 768. The median filtering is defined as $$p_i(m, n) = \begin{cases} \text{median}(C_i, m, n, S, T)|_{\text{median}(C_i, m, n, S, T) > T_{Low}} & \text{(Equation 1)} \\ 0|_{\text{otherwise}} \end{cases}$$

where $T_{Low}$ is a predefined threshold. An exemplary value for $T_{Low}$ is 20. S and T are the width and height of the median operation window. Exemplary values for S and T are 3 and 3. This operation is similar to the traditional process of trimmed median filtering well known to people skilled in the art. Notice that the purpose of the median filtering in the present invention is not to improve the visual quality of the input image as traditional image processing does; rather, it is to reduce the influence of a patch or patches of pixels that have very low intensity values at the threshold detection stage 906. A patch of low intensity pixels is usually caused by a limited illumination power and a limited viewing distance of the in vivo imaging system as it travels down to an opening of an organ in the GI tract. This median filtering operation also effectively reduces noises.

In color transformation step 904, after the media filtering, $I_{RGB}$ is converted to a generalized RGB image, $I_{gRGB}$, using the formula:

$$\overline{p}_j(m, n) = \frac{p_j(m, n)}{\sum_i p_i(m, n)} \quad \text{(Equation 2)}$$

where $p_i(m, n)$ is a pixel of an individual image plane i of the median filtered image $I_{RGB}$. $\overline{p}_i(m, n)$ is a pixel of an individual image plane i of the resultant image $I_{gRGB}$. This operation is not valid when $$\sum_i p_i(m, n) = 0,$$

and the output, $\overline{p}_i(m,n)$, will be set to zero. The resultant three new elements are linearly dependent, that is, $$\sum_j \overline{p}_j(m, n) = 0,$$

so that only two elements are needed to effectively form a new space that is collapsed from three dimensions to two dimensions. In most cases, $\overline{p}_1$ and $\overline{p}_2$, that is, generalized R and G, are used. In the present invention, to detect a telangiectasia 804, the converted generalized R component is needed. Image 822 in FIG. 8 displays the converted generalized R component of the image 802. Clearly, pixels in region 824 of image 822 have distinguishable values comparing to pixels in the background region. Therefore, a simple thresholding operation 906 can separate the pixels in the foreground (i.e., telangiectasia 824) from the background.

Figure 7A:
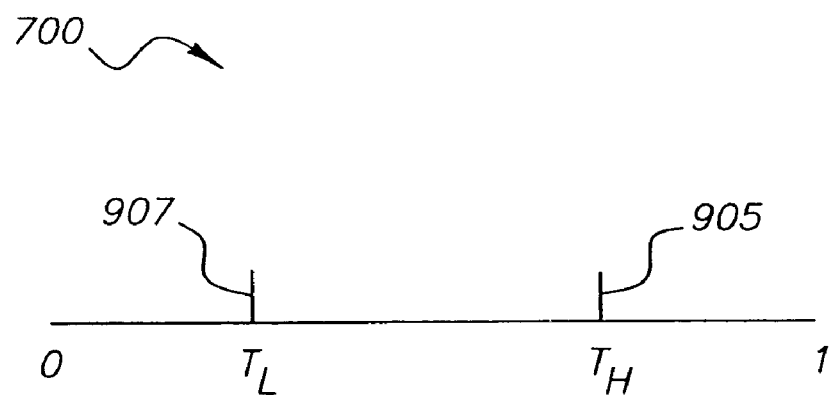
FIGS. 7a and 7b are one dimensional and two dimensional graphs, respectively, illustrating thresholding operations.

It is not a trivial task to parameterize the sub-regions of thresholding color in (R, G, B) space. With the help of color transformation 904, the generalized R color is identified to be the parameter to separate a disease region from a normal region. Referring to FIG. 7A, a one-dimensional graph 700 of the generalized R color of disease region pixels and the normal region pixels based on a histogram analysis provides useful information for partitioning the disease region pixels and the normal region pixels. The histogram is a result of a supervised learning of sample disease pixels and normal pixels in the generalized R space. A measured upper threshold parameter $T_H$ 905 (part of 534, see FIG. 5) and a measured lower threshold parameter $T_L$ 907 (part of 534, see FIG. 5) obtained from the histogram are used to determine if an element $\overline{p}_1(m, n)$ is a disease region pixel (foreground pixel) or a normal region pixel:

$$b(m, n) = \begin{cases} 1 & \text{if } T_L < \overline{p}_1(m, n) < T_H \\ 0 & \text{else} \end{cases} \quad \text{(Equation 3)}$$

where b(m, n) is an element of a binary image $I_{Binary}$ that has the same size as $I_{gRGB}$. Exemplary value for $T_L$ is 0.55, and exemplary value for $T_H$ is 0.70. Thus, FIG. 7A illustrates the thresholding operation range.

Referring to FIGS. 8A-8D and FIG. 9, Image 832 is an exemplary binary image $I_{Binary}$ of image 802 after the thresholding operation 906. Pixels having value 1 in the binary image $I_{Binary}$ are the foreground pixels. Foreground pixels are grouped in foreground pixel grouping step 908 to form clusters such as cluster 834. A cluster is a non-empty set of 1-valued pixels with the property that any pixel within the cluster is also within a predefined distance to another pixel in the cluster. Step 908 groups binary pixels into clusters based upon this definition of a cluster. However, it will be understood that pixels may be clustered on the basis of other criteria.

Under certain circumstances, a cluster of pixels may not be valid. Accordingly, a step of validating the clusters is needed. It is shown in FIG. 9 as cluster validation step 910. A cluster may be invalid if it contains too few binary pixels to acceptably determine the presence of an abnormality. For example, if the number of pixels in a cluster is less than V, then this cluster is invalid. Example V value could be 3. If there exists one or more valid clusters, an alarm signal will be generated and sent to OR gate 608, shown in FIG. 6. This alarm signal is also saved to the examination bundlette 220 for record.

Note that in Equation 1, pixels, $p_i(m, n)$, having value less than $T_{Low}$ are excluded from the detection of abnormality. A further explanation of the exclusion is given below for conditions other than the facts stated previously.

Figure 10A:
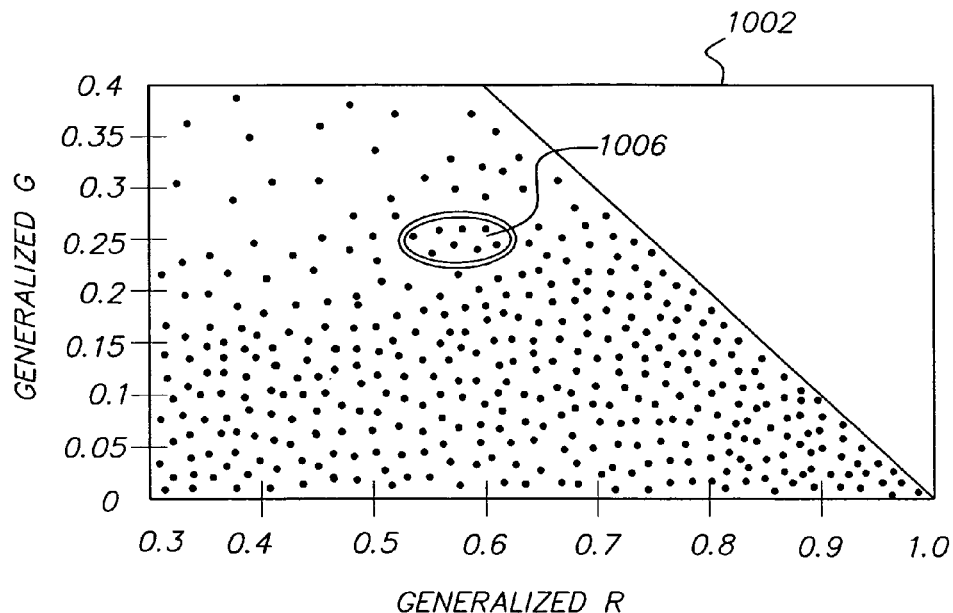
FIGS. 10A and 10B are illustrations of two graphs of generalized RG space of the present invention.
Figure 10B:
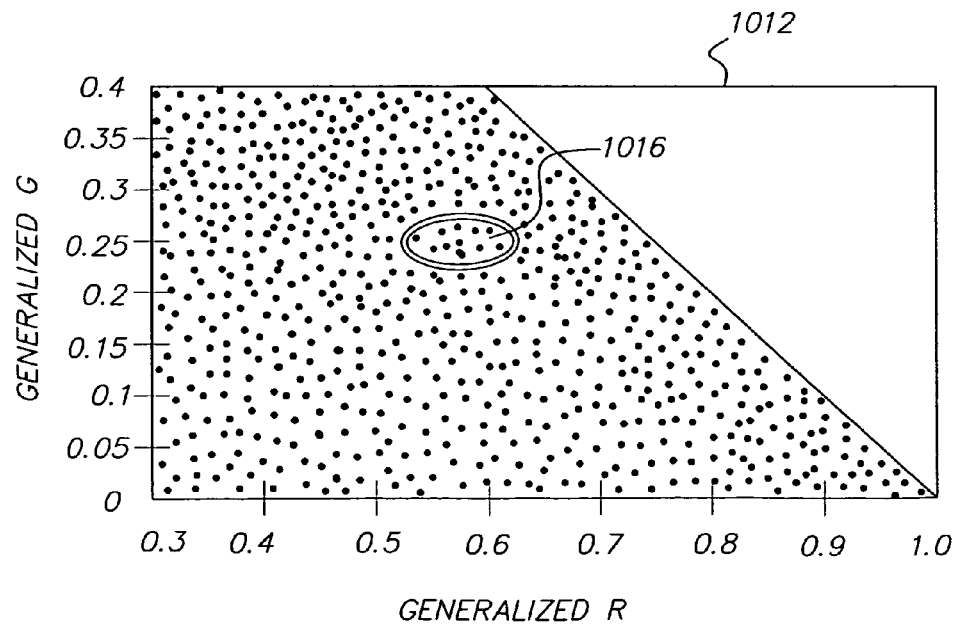

Referring to FIGS. 10A and 10B, there are two graphs 1002 and 1012, respectively, showing a portion of the generalized RG space. At every point in the generalized RG space, a corresponding color in the original RGB space fills in. In fact, the filling of original RGB color in the generalized RG space is a mapping from the generalized RG space to the original RGB space. This is not a one-to-one mapping. Rather, it is a one-to-many mapping, meaning that there could be more than one RGB colors that are transformed to a same point in the generalized space. Graphs 1002 and 1012 represent two of a plurality of possible mappings from the generalized RG space to the original RGB space.

Now in relation to the abnormality detection problem, region 1006 in graph 1002 indicates the generalized R and G values for a disease spot in the gastric fold, and region 1016 in graph 1012 does the same. Region 1006 maps to colors belonging to a disease spot in the gastric fold in a normal illumination condition. On the other hand, region 1016 maps to colors belonging to places having low reflection in a normal illumination condition. Pixels having these colors mapped from region 1016 are excluded from further consideration to avoid frequent false alarms.

Figure 7B:
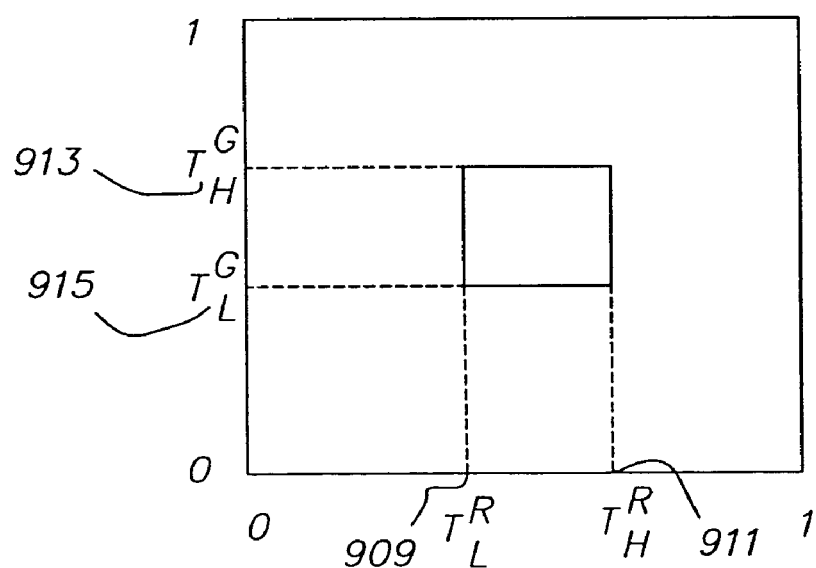

Also note that for more robust abnormality detection, as an alternative, threshold detection 906, in FIG. 9, can use both generalized R and G to further reduce false positives. In this case and referring to a two-dimensional graph 702 shown in FIG. 7B, the upper threshold parameter $T_H$ 905 (shown in FIG. 7A) is a two-dimensional array containing $T_H^G$ 913 and $T_H^R$ 911 for generalized G and R respectively. Exemplary values are 0.28 for $T_H^G$, and 0.70 for $T_H^R$. At the same time, the lower threshold parameter $T_L$ 907 (shown in FIG. 7A) is also a two-dimensional array containing $T_L^G$ 915 and $T_L^R$ 909 for generalized G and R respectively. Exemplary values are 0.21 for $T_L^G$, and 0.55 for $T_L^R$. In a transformed in vivo image $I_{gRGB}$, if the elements $\overline{p}_1(m, n)$ and $\overline{p}_2(m, n)$ of a pixel are between the range of $T_L^R$ and $T_H^R$ and the range of $T_L^G$ and $T_H^G$, then the corresponding pixel b(m, n) of the binary image $I_{Binary}$ is set to one. Thus, FIG. 7B illustrates thresholding ranges for this operation.

Referring again to FIG. 4, illustrated is an exemplary embodiment of an examination bundlette processing hardware system 400 useful in practicing the present invention including a template source 401 and an RF receiver 412. The template from the template source 401 is provided to an examination bundlette processor 402, such as a personal computer, or work station such as a Sun Sparc™ workstation. The RF receiver 412 passes the examination bundlette 220 to the examination bundlette processor 402. The examination bundlette processor 402 preferably is connected to a CRT display 404, an operator interface such as a keyboard 406 and a mouse 408. Examination bundlette processor 402 is also connected to computer readable storage medium 407. The examination bundlette processor 402 transmits processed digital images and metadata to an output device 409. Output device 409 can comprise a hard copy printer, a long-term image storage device, and/or a connection to another processor. The examination bundlette processor 402 is also linked to a communication link 414 or a telecommunication device connected, for example, to a broadband network.

It is well understood that the transmission of data over wireless links is more prone to requiring the retransmission of data packets than wired links. There is a myriad of reasons for this, a primary one in this situation is that the patient moves to a point in the environment where electromagnetic interference occurs. Consequently, it is preferable that all data from the examination bundle 200 be transmitted to a local computer with a wired connection. This has additional benefits, such as the processing requirement for image analysis is easily met.

Figure 16:
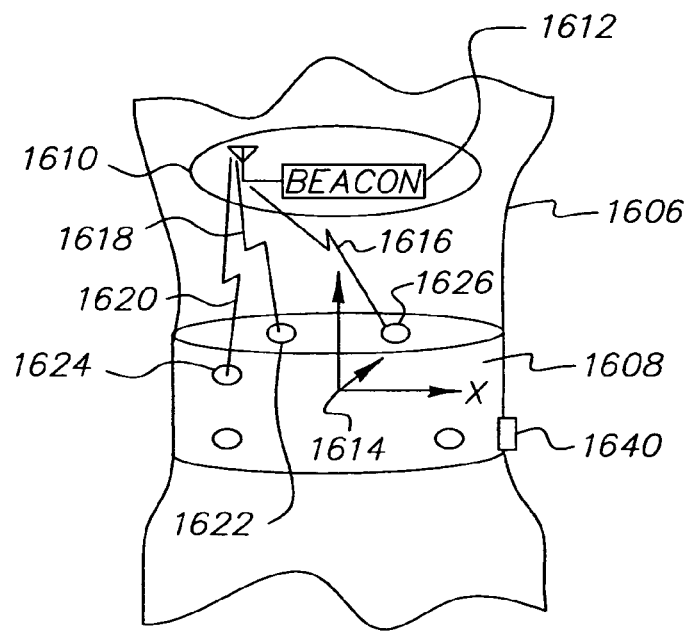
FIG. 16 is a prior art illustration of in vivo imaging capsule location finding.

Referring to FIG. 16, the primary role of the data collection device on a patient's belt 1608 is not burdened with image analysis. It is reasonable to consider such an operating system as a standard local area network (LAN). A recorder 1640 on the patient's belt 1608 is one node on the LAN. Signal transmission, shown as signals 1616, 1618 and 1620, from the recorder 1640 on the patient's belt 1608 is initially transmitted to a local node on the LAN, such as antenna elements 1626, 1622, and 1624, that are enabled to communicate with the portable patient recorder 1640 and a wired communication network. A wireless communication protocol such as IEEE-802.11, or one of its successors, is implemented for this application. This is the standard wireless communications protocol and is one of many that may be implimented. It is clear that the examination bundle 200 is stored locally within the recorder 1640 on the patient's belt 1608, as well as at a beacon 1612 in wireless contact with the recorder 1640 on the patient's belt 1608. However, while this is preferred, it will be appreciated that this is not a requirement for the present invention, only a single preferred operating situation. In general, a second node on the LAN has fewer limitations than the first node, as it has a virtually unlimited source of power, and weight and physical dimensions are not as restrictive as on the first node. Consequently, it is preferable for the image analysis to be conducted on the second node of the LAN. Another advantage of the second node is that it provides a "back-up" of the image data in case some malfunction occurs during the examination. When this node detects a condition that requires the attention of trained personnel, then this node system transmits to a remote site where trained personnel are present, a description of the condition identified, the patient identification, identifiers for images in the Examination Bundle, and a sequence of pertinent Examination Bundlettes. The trained personnel can request additional images to be transmitted, or for the image stream to be aborted if the alarm is declared a false alarm.

Using the above procedures or other methods, multiple passes of in vivo images can be obtained for a same person at different times for treatment assessment and disease progress examination. To achieve an efficient diagnosis, a diagnostic alignment of in vivo images from different passes is required. The procedures of diagnostic alignment of multiple in vivo image sequences are discussed below.

Figure 11:
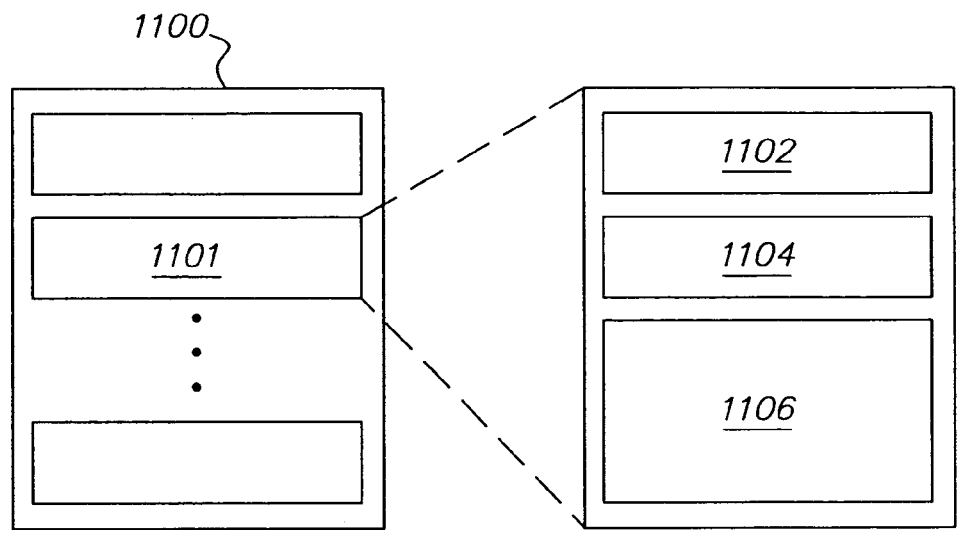
FIG. 11 is an illustration of GI atlas.
Figure 14:
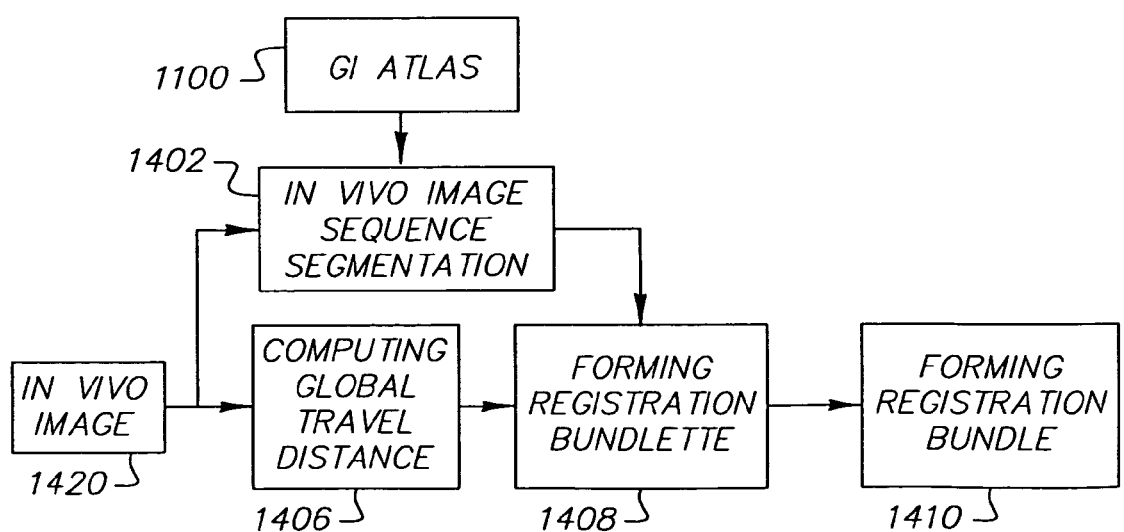
FIG. 14 is a flowchart illustrating registration bundlette and registration bundle formation;.

FIG. 11 illustrates the GI atlas 1100 that is provided to the classification engine "in vivo image sequence segmentation" 1402 of FIG. 14. The GI atlas 1100 is defined to be a list of anatomical structures, along with any pertinent characterization data for each individual anatomical structure. In the preferred embodiment, the list of anatomical structures includes the mouth, pharynx, esophagus, cardiac orifice, stomach, pylorus, duodenum, jejunum, ileum, ileocecal valve, cecum, colon, rectum, and anus. This list is not restrictive, however; other embodiments may include a subset of these anatomical structures, a more detailed set of anatomical structures, or a combination of structures (e.g., small intestine instead of duodenum, jejunum, and ileum). For a specific anatomical structure 1101, pertinent characterization data may include a structure label (or anatomical identity) 1102, non-image specific characterization data 1104, and image specific characterization data 1106. The structure label 1102 (anatomical identity) can simply be the anatomical name of the structure, such as mouth, pharynx, etc., or an index or key denoting the structure. For multiple passes diagnostic alignment, the structure label or the anatomical identity could be an integer starting from 0, ending at $N_a-1$, where $N_a$ is the number of different anatomical structures identified. Characterization data can include any type of data that describes or characterizes the anatomical structure. For example, non-image specific characterization data 1104 can include the average length or size of the structure, average relative position of the structure along the GI tract and/or with respect to other anatomical structures, average pH, temperature, and pressure levels of the structure, average motility characteristics of the structure, etc. Image specific characterization data 1106 can include representative images of the anatomical structure captured from various positions and orientations, and from various illumination levels, color and/or texture distributions or features of representative images of the structure, etc. Characterization data is not limited to the specific types of data described herein; rather, any data deemed pertinent to the identification of anatomical structure can be included in the non-image specific or image specific characterization data.

Figure 12:
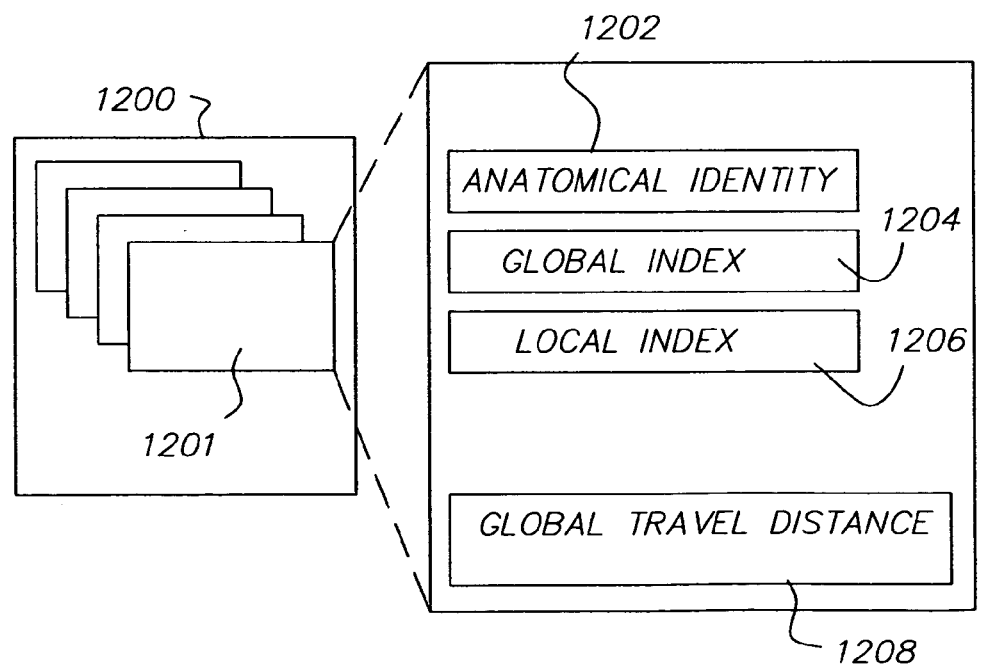
FIG. 12 is an illustration of registration bundle and registration bundlette of the present invention.

For clarity, a registration bundle 1200 is defined and shown in FIG. 12. Registration bundle 1200 is used in multiple passes registration or diagnostic alignment for in vivo images. It will be clear later that most of the information contained in registration bundle 1200 is also found in examination bundle 200.

The basic element of the registration bundle 1200 is a registration bundlette 1201. The number of elements in the registration bundle 1200 is the same as the number of in vivo images captured during the course of imaging the entire GI tract.

Figure 13A:
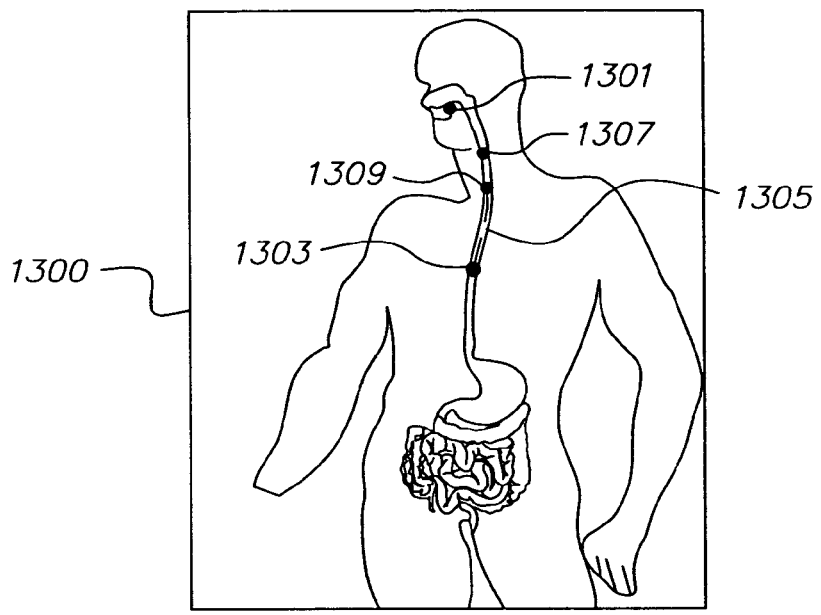
FIGS. 13A and 13B are illustrations of a GI tract and two passes of an anatomical structure, respectively.
Figure 13B:
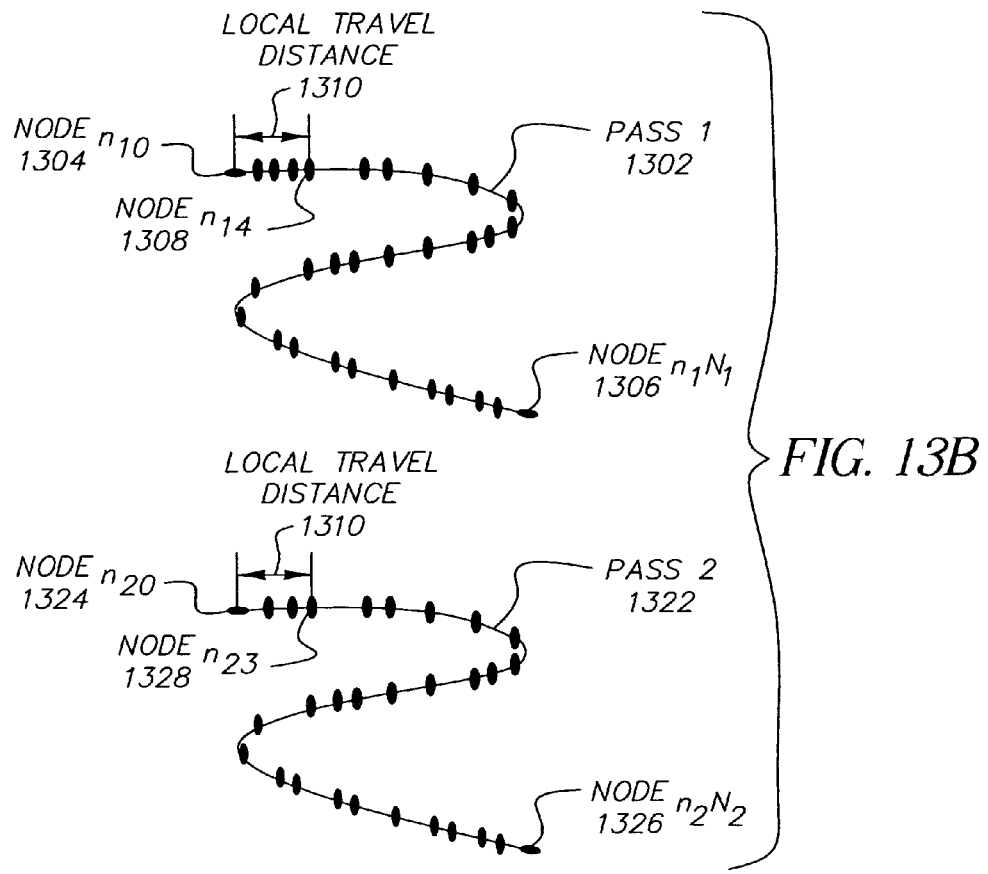

The registration bundlette 1201 contains anatomical identity 1202 (the same as the structure label 1102), global index 1204, local index 1206, and global travel distance 1208. As aforementioned, the exemplary representation of an anatomical identity 1202 is an integer running from 0 to $N_a-1$, where $N_a$ is the number of anatomical structures identified. The global index 1204 is the sequence number of the in vivo image. The global index 1204 is particularly useful in the real-time abnormality detection when a physician is prompted by the alarming signal and the physician wants to consult corresponding images in a pass completed previously. The local index 1206 is an index used for each individual anatomical structure. Examples of local indexing are shown in FIGS. 13A and 13B. Picture 1300 is a sketch of a human GI tract. Pass 1 (1302) and pass 2 (1322) are example sketches of an anatomical structure (e.g. small intestine) from two passes. Pass 1 (1302) runs from node $n_{10}$ (1304) to node $n_{1N_1}$ (1306). Pass 2 (1322) runs from node $n_{20}$ (1324) to node $n_{2N_2}$ (1326). An image captured in an anatomical structure is represented by an indexed node. For example, node $n_{10}$ (1304) is the first image taken in an anatomical structure in pass 1. So, the local index for $n_{10}$ (1304) is 0. Node $n_{14}$ (1308) is the fifth image taken in the same anatomical structure in pass 1. The local index for $n_{14}$ (1308) is 4. Similarly, node $n_{20}$ (1324) is the first image taken in an anatomical structure in pass 2. The local index for $n_{20}$ (1324) is 0. Node $n_{23}$ (1328) is the fourth image taken in the same anatomical structure in pass 2. The local index for $n_{23}$ (1328) is 3.

Global travel distance 1208 (see FIG. 12) is defined as the length of the path that the imaging capsule travels from a starting point such as the mouth 1301. The global travel distance 1208 may be computed by localizing the in vivo imaging system capsule in a three dimensional space. European Patent Application No. 1 260 176 A2, by Arkady Glukhovsky et al., published Nov. 27, 2002, and titled "Array System And Method For Locating An In Vivo Signal Source," and incorporated herein by reference, teaches a method for localizing an in vivo signal source using a wearable antenna array.

FIG. 16 shows the arrangement of such a design used in European Patent Application No. 1 260 176 A2. The antenna array belt 1608 is fitted such that it may be wrapped around a patient's torso 1606 and attached to a signal recorder 1640. Each of the antenna elements such as 1622, 1624, and 1626 in the array may connect via coaxial cables to a connector, which connects to the recorder 1640.

The data recorder 1640 also has a receiver, a signal strength measurement unit, a processing unit, and an antenna selector. The signal strength measurement unit may measure the signal strength of signals received by the receiver from each of the antenna elements such as 1622, 1624, and 1626, and the processing unit may perform calculations to correlate the received signal with an estimated location of the source of the signal. The location is calculated with respect to a three-dimensional coordinate reference system 1614.

The capsule 1610 contains a beacon 1612 sending out an intermittent beacon signal to the antenna elements such as 1622, 1624, and 1626. The distance values may be calculated by a conventional processing unit based on signal strength measurements preformed by a conventional signal strength measurement unit; both of which are known in the art and are not illustrated herein.

Alternatively, global travel distance 1208 (see FIG. 12) may be obtained by analyzing a position disparity (in pixels) of a same feature point in two neighboring images. Position disparities not caused by camera rotations around the optical axis are cumulated from the first image. The accumulated disparities (pixels) are regarded as global travel distance 1208. Technologies such as image motion analysis and optical flow analysis may be used.

An exemplary global travel distance 1208 is illustrated in FIG. 13 from point 1301 to point 1303. Notice that the path 1305 from point 1301 to point 1303 is not a straight line. That is, global travel distance 1208 is not calculated as a shortest distance between two points in the three dimensional space 1614 shown in FIG. 16. Rather, global travel distance 1208 is a cumulative distance of all the points involved. Thus, exemplary global travel distance 1208 from point 1301 to point 1303 is the sum of all local travel distances from points 1301 to 1307, 1307 to 1309 and 1309 to 1303. Also notice that the local travel distance between two neighboring points is an Euclidean distance in the three dimensional space if the method disclosed in European patent Application 1 260 176 A2 is used.

Now, referring to FIG. 14, a process of forming registration bundlette 1201 (in step 1408 of forming registration bundlette) and registration bundle 1200 (in step 1410 of forming registration bundle) is shown.

With reference to FIG. 14, in vivo images 1420 (from in vitro RF receiver 308) are input to a step of in vivo image segmentation 1402 to classify and group images according to anatomical structure with the knowledge of GI atlas 1100.

Referring to both FIGS. 12 and 14, the classification results of step 1402 will be saved as anatomical identities 1202. Exemplary representation of an anatomical identity could be an integer. For example, an image is classified as part of a mouth, the associated anatomical identity is assigned a zero. In a step to identify terminal nodes for anatomical structures where an image is identified as the beginning of an anatomical structure, the computation of global travel distance 1406 is zero. The identification of the beginning and end of a structure is accomplished based on anatomical identities 1202 obtained from step 1402. When a new anatomical identity is encountered, the corresponding image (or node see FIG. 13) is marked as the beginning of a structure. Simultaneously, the image immediately preceding the image marked as the beginning of a new structure is identified as the end of the current structure.

In a step of computing global travel distance 1406, the method of computing cumulative travel distance described in the previous paragraphs is used. The result of step 1406 for each image is saved as global travel distance 1208. The image index of an image in the image sequence 1420 is saved as global index 1204.

Figure 15A:
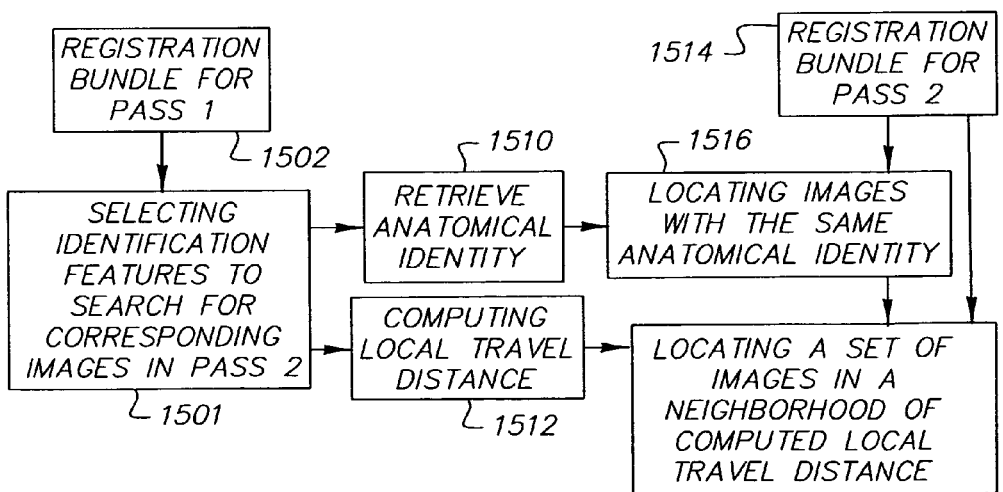
FIGS. 15A and 15B are flowcharts illustrating operating steps for multiple passes diagnostic alignment.
Figure 15B:
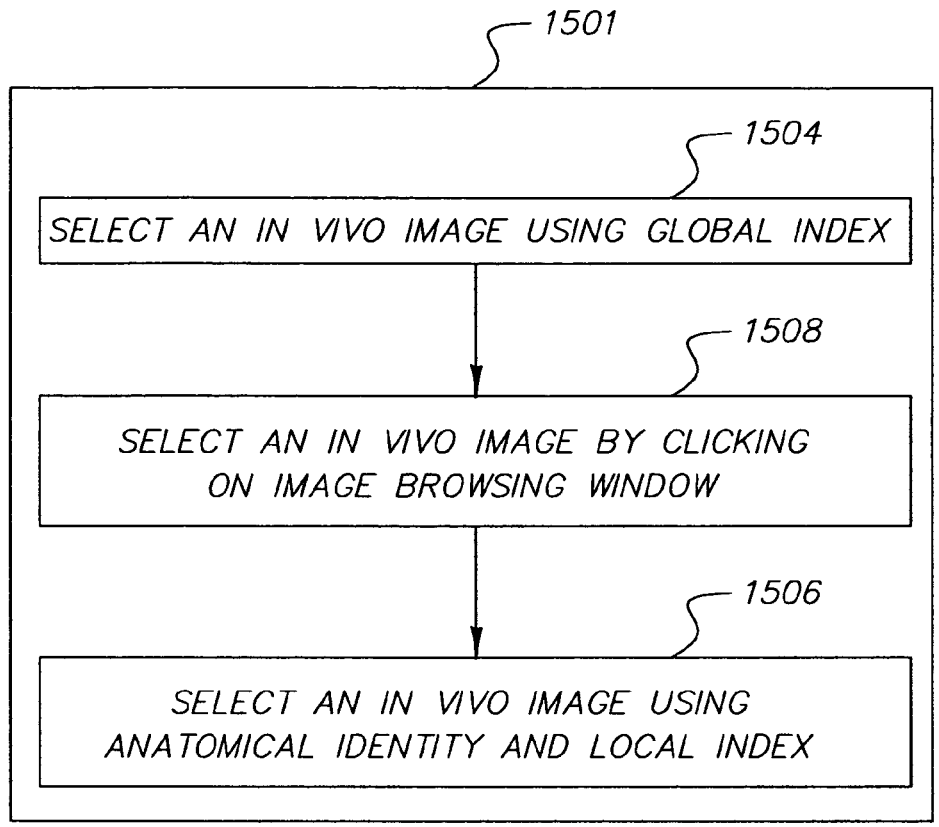

With reference to both FIGS. 15A and 15B, two exemplary multiple passes are presented; namely, registration pass 1 (1502) and registration pass 2 (1514). Note that pass 1 (1502) is not necessarily taken before pass 2 (1514). A health care worker starts the diagnostic process by selecting identification features in step 1501. FIG. 15B shows that there are three options for selecting a feature or features to locate images in pass 2. When option 1504 or option 1508 is selected, global index 1204 is used. Global index 1204 (shown in FIG. 12) may be used directly to locate corresponding images in pass 2 (1514). However, using global index 1204 alone is less accurate than local features if they are available. Therefore in step 1510, a corresponding anatomical identity number 1202 (FIG. 12) is retrieved from registration bundle 1200 (FIG. 12) of pass 1 and sent to step 1516 to locate images with the same anatomical identity in pass 2. Usually, an anatomical structure contains hundreds of images. To narrow down the search, a step of computing local travel distance 1512 is taken.

Referring back to FIG. 13B, an example of computing local travel distance is shown. A local travel distance of an image of interest in an anatomical structure is computed by subtracting the global travel distance of the image marked as the beginning of the anatomical structure from the global distance of the image of interest. For example, the local travel distance 1310 is a measure of the distance from the image at the start node $n_{10}$ (1304) of an anatomical structure to an image at node $n_{14}$ (1308).

After the local travel distance is computed, searching of corresponding images in pass 2 becomes more precise. An example is shown in FIG. 13B. Pass 2 (1322) is identified as a same anatomical structure as pass 1 (1302) in step 1516 (FIG. 15A). A node, node $n_{23}$ (1328), is located (measured from the starting node, node $n_{20}$ (1324)) in pass 2 using the computed local travel distance in pass 1, local travel distance 1310.

In most cases, there will never be a precise alignment. In other words, an image in pass 1 will never find an image in pass 2 at the same location. So for a practical diagnostic alignment, it is better to retrieve a set of images in pass 2 around an image believed to be the image having the same or approximately the same local travel distance from the start of the anatomical structure. This is done in a step of locating a set of images in a neighborhood of computed local travel distance (1518) shown in FIG. 15A. For example, the neighboring images around node $n_{23}$ (1328) will be retrieved for inspection.

Referring back to FIGS. 12, and 15A and 15B, when option 1506 is selected, anatomical identity 1202 and local index 1206 are used. In this case, step 1510 is skipped for a faster search. The local index helps to compute the local travel distance by using associated global travel distance 1208. The remaining procedures are the same as described above.

The method of diagnostic alignment discussed so far is applicable to real-time operation as well. As depicted in FIG. 3, when the health care worker is prompted by an alarm signal from step 310, she/he can perform the diagnostic alignment procedure to find corresponding images in previous passes (if they exist) for better diagnosis. The diagnostic alignment can be performed locally at local site 314 or remotely at remote site 316.

For people skilled in the art, it is understood that the real-time abnormality detection algorithm of the present invention can be included directly in the design of an on board in vivo imaging capsule and processing system.

The invention has been described in detail with particular reference to certain preferred embodiments thereof, but it will be understood that variations and modifications can be effected within the spirit and scope of the invention.

PARTS LIST 5 in vivo video camera system
100 storage unit
102 data processor
104 camera
106 image transmitter
108 image receiver
110 image monitor
112 capsule
200 examination bundle
202 image packet
204 general metadata
208 in vivo image
210 image specific metadata
212 image specific collection data
214 image specific physical data
216 inferred image specific data
220 examination bundlette
300 in vivo imaging system
302 in vivo image acquisition
304 forming examination bundlette
306 RF transmission
308 RF receiver
310 abnormality detection
312 communication connection
314 local site
316 remote site
320 in vitro computing device
400 examination bundlette processing hardware system
401 template source
402 examination bundlette processor
404 image display
406 data and command entry device
407 computer readable storage medium
408 data and command control device
409 output device
412 RF receiver
414 communication link
502 threshold detector
504 threshold detector
506 threshold detector
507 threshold detector
508 priori knowledge
510 examination bundlette processing
512 input (pH)
514 input (pressure)
516 input (temperature)
518 input (impedance)
511 threshold
515 threshold
517 threshold
519 threshold
522 OR gate
524 output
532 image
534 template
536 multi-feature detector
602 image feature examiner
604 image feature examiner
606 image feature examiner
608 OR gate
700 graph of thresholding operation range
702 graph
802 color in vivo image
804 red spot (telangiectasia)
812 R component image
814 spot
816 dark area
822 generalized R image
824 spot
832 binary image
834 spot
901 image
902 filtering
904 color transformation
905 threshold
906 threshold detection
907 threshold
908 foreground pixel grouping
909 lower threshold for generalized R
910 cluster validation
911 upper threshold for generalized G
913 upper threshold for generalized R
915 lower threshold for generalized G
1002 generalized RG space graph
1006 region
1012 generalized RG space graph
1016 region
1100 GI atlas
1101 specific anatomical structure 1102 structure label
1104 non-image specific characterization data
1106 image specific characterization data
1200 Registration Bundle
1201 Registration Bundlette
1202 anatomical identity
1204 global index
1206 local index
1208 global travel distance
1300 picture
1301 location
1302 pass 1
1303 location
1304 node
1305 path
1306 node
1307 location
1308 node
1309 location
1310 local travel distance
1322 pass 2
1324 node
1326 node
1328 node
1402 in vivo image sequence segmentation
1406 computing global travel distance
1408 forming registration bundlette
1410 forming registration bundle
1420 in vivo image
1501 selecting identification features
1502 registration bundle
1504 select an image using global index
1506 selecting an image using anatomical identity and local index
1508 select an image
1510 retrieve anatomical identity
1512 computing local travel distance
1514 registration bundle
1516 locating images with the same anatomical identity
1518 locating a set of images
1606 torso
1608 belt
1610 capsule
1612 beacon
1614 three-dimensional coordinate system
1616 signal
1618 signal
1620 signal
1622 antenna array element
1624 antenna array element
1626 antenna array element
1640 recorder

What is claimed is:

1. A digital image processing method for aligning in vivo images from multiple passes of a gastrointestinal tract to aid in diagnosing gastrointestinal disease, comprising the steps of:
   a) conducting multiple passes of in vivo imaging within the gastrointestinal tract;
   b) forming a registration bundle of metadata for each of the multiple passes;
   c) identifying features of an in vivo image using digital image processing that enable diagnosis of the gastrointestinal disease;
   d) automatically selecting possible image features of an in vivo image from the registration bundle, associated with one pass, using algorithmic classification;
   e) retrieving a global index and an anatomical index and computing local travel distance based on said global index and said anatomical index; and
   f) retrieving corresponding images in a neighborhood of said computed local travel distance from another pass based on prior selection of the possible image features.

2. The digital image processing method claimed in claim 1, wherein forming a registration bundle of metadata, includes the steps of:
   b1) retrieving an anatomical identity label associated with the gastrointestinal tract;
   b2) retrieving a global index label corresponding to each in vivo imaging pass;
   b3) retrieving a local index label with respect to a specific anatomical section within the gastrointestinal tract;
   b4) calculating global travel distance within the gastrointestinal tract;
   b5) forming at least one registration bundlette from information in steps b1-b4; and
   b6) forming a registration bundle from the at least one registration bundlette, wherein the at least one registration bundlette includes at least a combination of the anatomical identity label, the global index label, the local index label, and the global travel distance.

3. The digital image processing method claimed in claim 1, wherein selection of the possible indexed features includes the step of selecting an in vivo image using a global index.

4. The digital image processing method claimed in claim 1, wherein selection of the possible indexed features includes the step of selecting an in vivo image by browsing a plurality of images.

5. The digital image processing method claimed in claim 1, wherein selection of the possible indexed features includes the step of selecting an in vivo image using an anatomical identity and a local index.

6. A digital image processing method for aligning in vivo images from multiple passes of a gastrointestinal tract to aid in diagnosing gastrointestinal disease, comprising the steps of:
   a) conducting multiple passes of in vivo imaging within the gastrointestinal tract:
   b) forming a registration bundle of metadata for each of the multiple passes;
   c) identifying features of an in vivo image using digital image processing that enable diagnosis of the gastrointestinal disease;
   d) automatically selecting possible image features of an in vivo image from the registration bundle, associated with one pass, using algorithmic classification;
   e) retrieving corresponding images from another pass based on prior selection of the possible image features;
   wherein selection of the possible indexed features includes the step of selecting an in vivo image using a global index;
   wherein retrieving corresponding images from another pass based on prior selection of the in vivo image using the global index further includes the steps of:
   d1) retrieving anatomical identity based on a global index;
   d2) computing a local travel distance using a global travel distance and the anatomical identity;
   d3) locating images corresponding to the anatomical identity; and
   d4) locating a set of images in a neighborhood of computed local travel distance.

7. A digital image processing method for aligning in vivo images from multiple passes of a gastrointestinal tract to aid in diagnosing gastrointestinal disease, comprising the steps of:
- a) conducting multiple nasses of in vivo imaging within the gastrointestinal tract;
- b) forming a registration bundle of metadata for each of the multiple passes;
- c) identifying features of an in vivo image using digital image processin that enable diagnosis of the gastrointestinal disease;
- d) automatically selecting possible image features of an in vivo image from the registration bundle, associated with one pass, using algorithmic classification;
- e) retrieving corresponding images from another pass based on prior selection of the possible image features;
- wherein selection of the possible indexed features includes the step of selecting an in vivo image by browsing a plurality of images;
- wherein retrieving corresponding images from another pass based on prior selection of the possible indexed features further includes the steps of:
  - d1) retrieving a global index;
  - d2) retrieving anatomical identity based on the global index;
  - d3) computing a local travel distance using a global travel distance and the anatomical identity;
  - d4) locating images corresponding to the anatomical identity; and
  - d5) locating a set of images in a neighborhood of computed local travel distance.

8. A digital image processing method for aligning in vivo images from multiple passes of a gastrointestinal tract to aid in diagnosing gastrointestinal disease, comprising the steps of:
- a) conducting multiple passes of in vivo imaging within the gastrointestinal tract;
- b) forming a registration bundle of metadata for each of the multiple passes;
- c) identifying features of an in vivo image using digital image processing that enable diagnosis of the gastrointestinal disease;
- d) automatically selecting possible image features of an in vivo image from the registration bundle, associated with one pass, using algorithmic classification; and
- e) retrieving corresponding images from another pass based on prior selection of the possible image features,
- wherein selection of the possible indexed features includes the step of selecting an in vivo image using an anatomical identity and a local index;
- wherein retrieving corresponding image) from another pass based on prior selection of the possible indexed features further includes the steps of:
  - d1) computing a local travel distance using a global travel distance and the anatomical identity;
  - d2) locating images corresponding to the anatomical identity; and
  - d3) locating a set of images in a neighborhood of computed local travel distance.

9. An in vivo imaging alignment and processing system, comprising:
- a) an image alignment processor for selecting and retrieving possible indexed features of a plurality of in vivo images from multiple image capturing passes, wherein the possible indexed features enable one to correctly align the plurality of in vivo images from multiple image capturing passes according to images captured at substantially similar positions in a gastrointestinal tract based on a computed local travel distance based on a global index and an anatomical index, and images in a neighborhood of said computed local travel distance;
- b) a template source for detecting in vivo images that indicate a diseased gastrointestinal tract and sending the in vivo images to the image alignment processor;
- c) a display for displaying a plurality of aligned in vivo images;
- d) a means for transmitting the plurality of in vivo images;
- e) a means for storing metadata associated with the plurality of in vivo images;
- f) a means for communicating selected in vivo images across a network;
- g) a means for outputting the plurality of aligned in vivo images; and
- h) a user interactive means for inputting and/or controlling the metadata and/or the plurality of in vivo images.

* * * * *